United States Patent [19]

Kraemer et al.

[11] Patent Number: 5,357,975
[45] Date of Patent: Oct. 25, 1994

[54] DEVICE FOR MEASURING THE FLOW-VOLUME OF PULMONARY AIR

[75] Inventors: Richard Kraemer; Andreas Schibler, both of Berne, Switzerland

[73] Assignee: Isoraw S.A., Aubonne, Switzerland

[21] Appl. No.: 940,895

[22] PCT Filed: Feb. 28, 1992

[86] PCT No.: PCT/CH92/00040
§ 371 Date: Dec. 8, 1992
§ 102(e) Date: Dec. 8, 1992

[87] PCT Pub. No.: WO92/15246
PCT Pub. Date: Sep. 17, 1992

[30] Foreign Application Priority Data
Feb. 28, 1991 [GB] United Kingdom ............... 9104201

[51] Int. Cl.$^5$ .................................... A61B 5/091
[52] U.S. Cl. ............................................ 128/725
[58] Field of Search ....................... 128/716–730; 422/83–84, 92

[56] References Cited
U.S. PATENT DOCUMENTS
4,063,550 12/1977 Tiep .................................. 128/716
4,744,953 5/1988 Wolf et al. .

FOREIGN PATENT DOCUMENTS
0178042 4/1986 European Pat. Off. .

Primary Examiner—Angela D. Sykes
Attorney, Agent, or Firm—Woodard, Emhardt, Naughton Moriarty & McNett

[57] ABSTRACT

The apparatus is comprised of a connection conduit comprising a mouth piece at one of its extremities, a sound generator provided with a nose, as well as a digital time measuring unit. A tapping exhaust orifice allows to tap a portion of the expired air. The orifice has an opening which is adjustable by simply turning a cuff, screwed on the outside of the conduit. When the patient expires in the apparatus, only a well defined fraction of the airflow is directed towards the sound generator, the remainder being eliminated in the atmosphere through the tapping exhaust. The airflow which remains is directed through the sound generator wherein a well defined note is produced.

22 Claims, 5 Drawing Sheets

DEVICE FOR MEASURING THE FLOW-VOLUME OF PULMONARY AIR

The present invention relates to a device for measuring the flow-volume of pulmonary air breathed out by a subject.

BACKGROUND OF THE INVENTION

Flow-volume curves, conventional lung function tests, are widely used to measure airflow limitation, and hence the degree of bronchial obstruction of small bronchial airways in children and adults with lung diseases.

Figure 1:
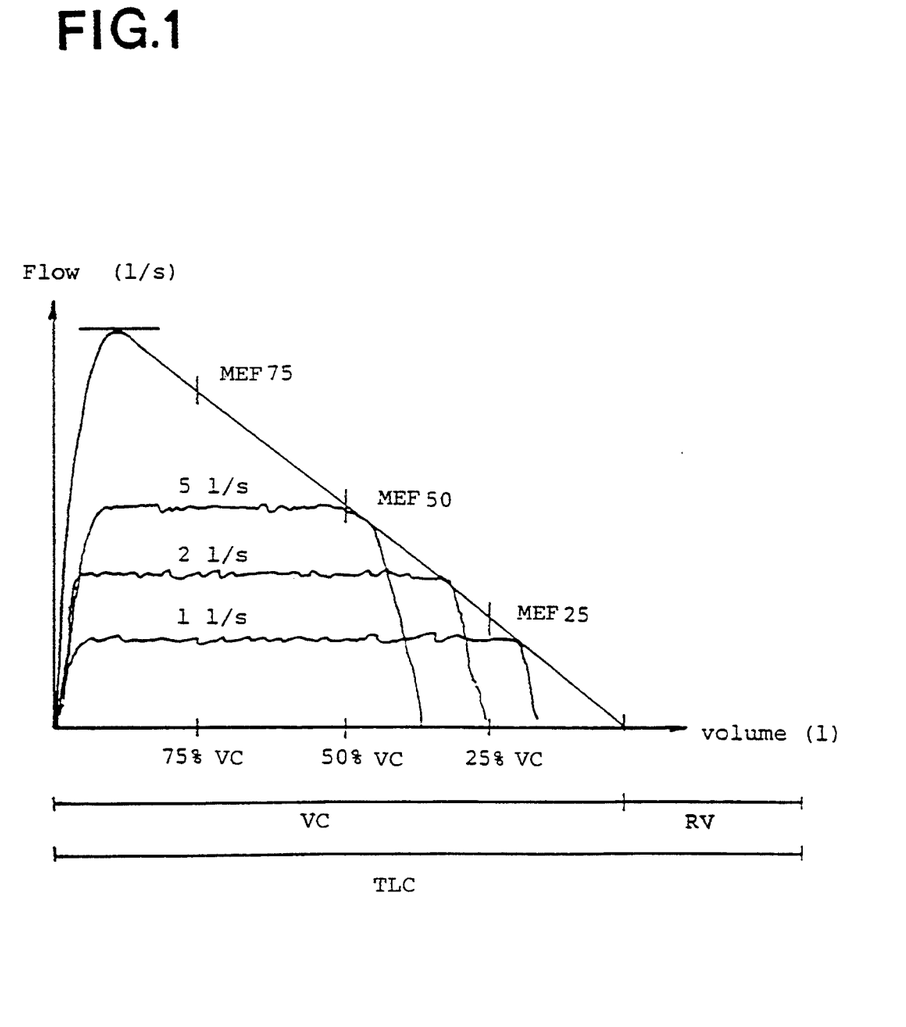
FIG. 1 shows a number of curves expressing the relationship of flow to volume of exhaled air, one of the curves having already been referred to, and the others being referred to below.

The upper trace in FIG. 1 of the accompanying drawings is a flow-volume curve produced by asking the subject to breathe in as much as possible until total lung capacity (TLC) is reached, and then to breathe out as quickly and as strongly as possible. The trace shows on the axes of abscisses changes in volume, measured from the total lung capacity (TLC) to residual volume (RV), the difference between them being defined as the vital capacity (VC). The ordinate indicates the changes in flow. In the first part of the curve, a high flow, the so called peak expiratory flow (PF) or "peak flow" is reached. Thereafter, the volume is displaced and the flow decreases in a healthy subject linearly from peak expiratory flow (PF) to residual volume (RV). The maximal expiratory flows at 75, 50 and 25% of vital capacity (VC), defined respectively as MEF75, MEF50 and MEF25 are standardized flows with respect to a well defined lung volume.

Specific diseases which are of concern in this field include wheezy bronchitis and asthma in children, bronchial asthma, cystic fibrosis and chronic obstructive lung disease in adults (COLD). All these illnesses are characterized by a decrease in the performance of the airways, leading to bronchial obstruction which progresses with age. Functionally, bronchial obstruction is characterized by airflow limitation. There is great interest in determining the magnitude of this decrease, in order to get objective information about the degree of functional impairment of the lungs, as well as the stability of the disease. The latter, however, can only be determined if day-to-day variations in airflow limitation are followed ambulatorily by home monitoring.

There is therefore a need to have a low-cost, simple medical device for the measurement of airflow, which is independent of electric supply, easy to use, but accurate in its assessment, and which provides objective data for medical interpretation by patients and doctors.

It is standard practice for pediatricians, general practitioners and internists to measure airflow limitation on an ambulatory basis with devices such the Wright peak-flow meter or the Pulmonary Achievement Trainer, when measuring airways obstruction in patients with lung disease. The former is described in GB-A-1160669, and the latter in US-A-3826247. In such devices the maximum flow of air which a person can produce when exhaling is measured in a cylindrical tube within which a piston or a plate is actuated by the entering air and displaced from its initial zero-position to a scaled distance reflecting the maximum flow breathed through. Practical use of such devices has shown that calibration in absolute terms is difficult, intra-individual variation is high and inter-individual comparisons are rather difficult. Application is therefore limited to long-term monitoring where the patient is its one control. Application is also restricted to measurements of maximum flow of air, and hence to measurements of peak expiration flow (peak-flow). In this context it must be recognized, that peak-flow measurements only are the tip of the iceberg, so to speak, of the underlying functional disorders, reflecting only processes in large airways, whereas other obstructions are sometimes more important. In addition, blowing flow-volume curves (including that for peak-flow measurement) by a particular subject require rather unnatural forced breathing maneuvers. There is considerable scientific work showing that after repeated forced breathing maneuvers test-induced bronchospasms can occur. In addition, especially in children and older patients considerable difficulties are encountered in blowing accurately reproducible flow-volume curves because of the limited cooperation of these patients.

The description of the prior art known up to today is related to various pulmonary disease such as wheezy bronchitis, bronchial asthma, cystic fibrosis both in adults and children, and chronic obstructive lung disease (COLD) in adults requiring careful analysis of the functional condition of a patient's lungs. By requiring the patient to blow into a diagnostic device, the functional conditions of the patient's lungs can be detected. However, in the past, there has been no simple but accurate working diagnostic device for bed-side use, and hence home use, which will inform the physician with a direct read-out about the functional condition of a patient's lungs during a predetermined period of therapy.

SUMMARY OF THE INVENTION

The purpose of the present invention is on the one hand to remedy these disadvantages and on the other hand to propose a measuring device of the flow-volume of pulmonary air breathed out by a subject, easily transportable and which allows the recording of data concerning the breathing of this subject.

To this end, the invention is concerned with a measuring device of the flow-volume of pulmonary air breathed out by a subject. Other features of the invention are set out below.

For using this device, the subject must inhale fully, then exhale gently, not in a forced fashion, through the mouthpiece of the device. It is found that a subject will automatically adjust his or her rate of exhalation to produce from the whistle a steady note of substantially constant amplitude, with the result that the rate of exhalation is substantially constant over the test, except at the beginning and end.

Based on repeated measurements at different rates of exhalation, flow-volume curve data can be calculated as described below. The measurements do not require forced breathing maneuvers.

In addition of the advantages already mentioned, the device of the present invention can be made with small dimensions, smaller than the Wright peak-flow meter or the Pulmonary Achievement Trainer. It can be carried like a pencil and can work independent of an electric supply.

Other advantages of the invention will become apparent from the description, given by way of example, which follows and refers to the attached drawing in which:

DESCRIPTION OF THE PREFERRED EMBODIMENTS

Figure 2:
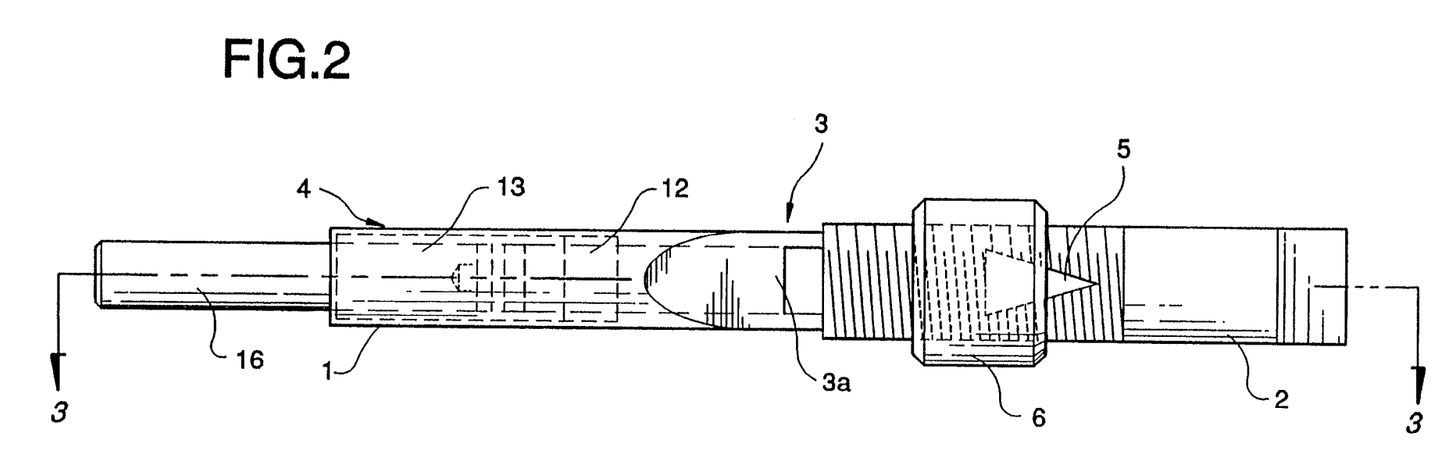
FIG. 2 is a plan view of one embodiment of a device according to the present invention.
Figure 3:
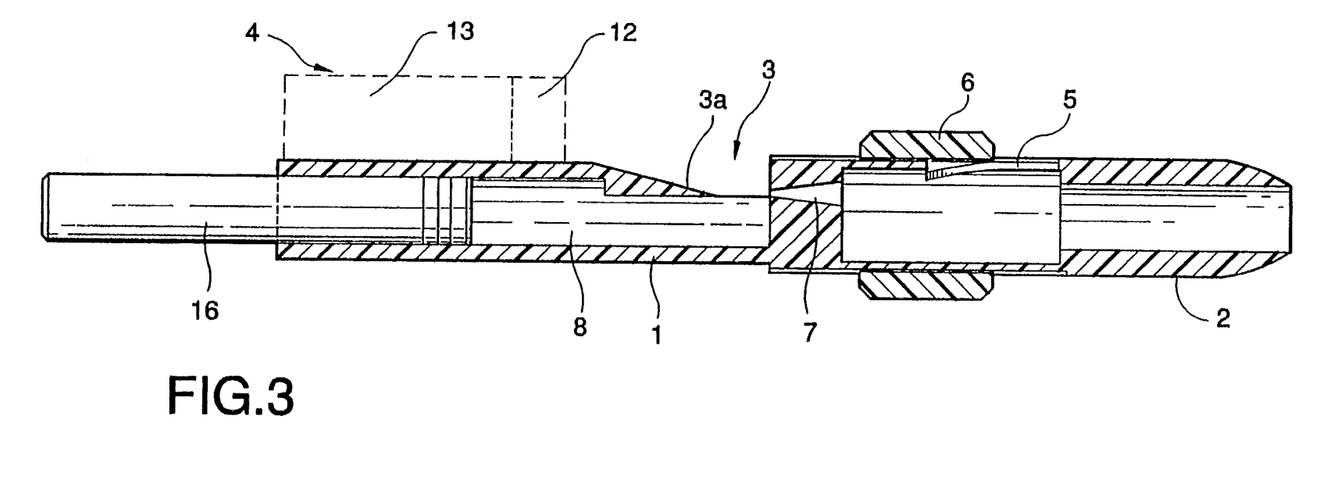
FIG. 3 is a longitudinal section taken on line 3—3 in FIG. 2.

The device represented in FIGS. 2 and 3 comprises a connecting duct 1 having a mouthpiece 2 at one end thereof, a sound generator 3 having a lip 3a, and a digital time measurement unit (DTMU) 4. Said unit 4 is shown only diagrammatically in FIGS. 2 and 3. The device, except for the time measurement unit, can be made of a translucent acrylic plastics material, the time measurement unit being preferably disconnectable, so that, after said unit has been disconnected, the device can be cleaned and sterilized. The mouthpiece 2 has a smaller diameter than the connecting duct 1. Its outlet end is oval-shaped for a better fit to the subject's mouth, changing toward the connecting duct 1 into a circular cross section. Optionally, and especially for use in infants, the mouthpiece can be replaced by a face mask. The connecting duct 1 is used to define the amount of air which is driven through the sound generator 3. The triangular by-pass outlet 5 provides a by-pass for the exhaled airflow. The outlet 5 can be closed to an adjustable extent by simply turning a cuff 6, which is screwthreaded on to the exterior of the duct 1. When a subject breathes through the device, only a well defined part of the airflow is directed to the sound generator 3, the rest being by-passed to the atmosphere through the outlet 5. The remaining airflow is directed through the sound generator 3 in which a well defined note is produced. The connecting duct 1 can be provided with a scale which can be calibrated using a pneumotachograph. By this means the airflow directed through the sound generator 3 can be defined in its absolute terms (liters/second).

The sound generator 3 is constructed according to the classical principles of the wind instrument known as a recorder. The airflow passes through a duct 7 and strikes the lip 3a, setting up resonance in a resonance chamber 8. The size (length and diameter) of the resonance chamber 8 defines the frequency of the note. According to an embodiment of the invention, a note with a frequency of 1650 Hertz is chosen. This frequency is precisely adapted to the main bandpass frequency of the time measurement unit (DTMU). The sensitivity of the sound generator 3, and hence the reproducibility of the volume measurements has been found to be critically dependent on the angle of the lip 3a. In particular, an angle of 12° enables a good note quality to be produced by a flow rate of as little as 0.1 l/s. Even at such a low flow rate it has been found that deviations of the flow rate of only ±5% were sufficient to prevent a good note being generated. It follows that the generation of such a note is an accurate indication that a particular flow rate has been achieved. In fact the flow rates actually involved when the device is used by a patient are 0.2 l/s and above. With such flow rates, the reproducibility is to be expected to be even better.

In order to permit an adjustment of the resonance frequency of the resonance chamber 8 to the desired level, the chamber can be provided with a sliding piston 16. When the adjustment is achieved, the piston is blocked. Of course, any other device permitting to varying the dimensions of the resonance chamber to adapt the frequency can be contemplated.

Figure 4:
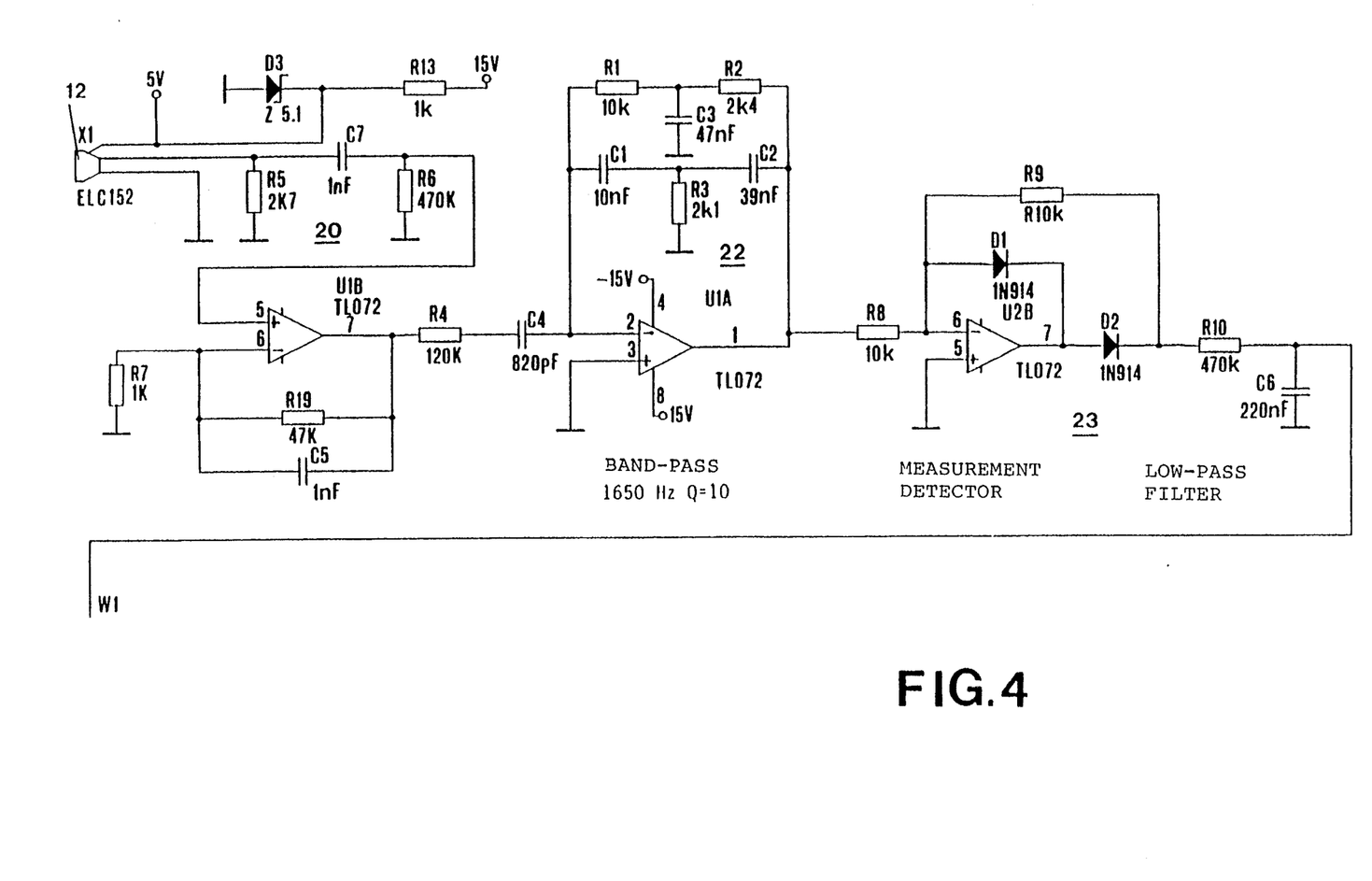
FIGS. 4, 4a and 4b together form a single view of an example of a circuit diagram showing the circuit used in the detector which is shown in FIGS. 2 and 3.
Figure 4A:
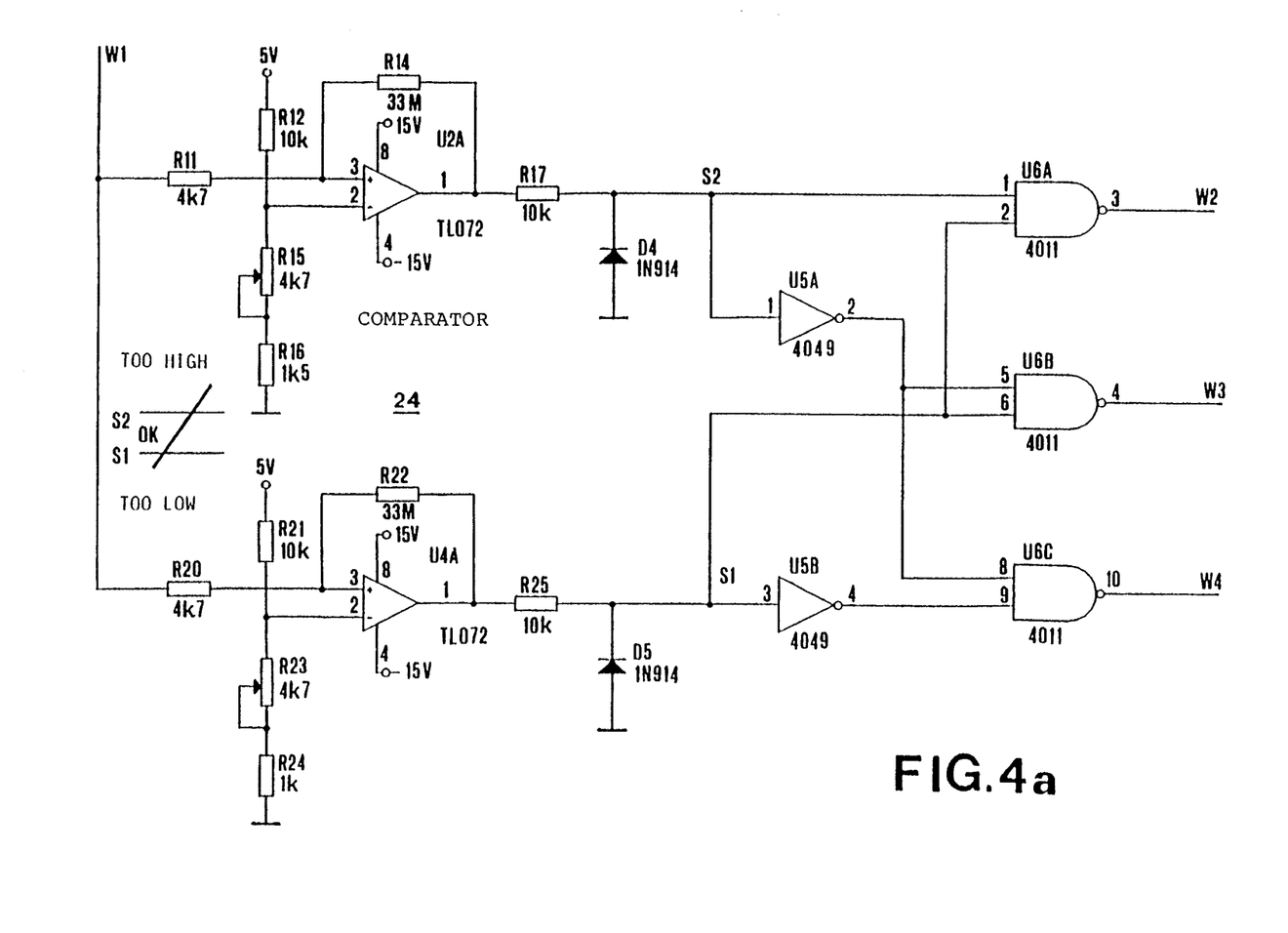
Figure 4B:
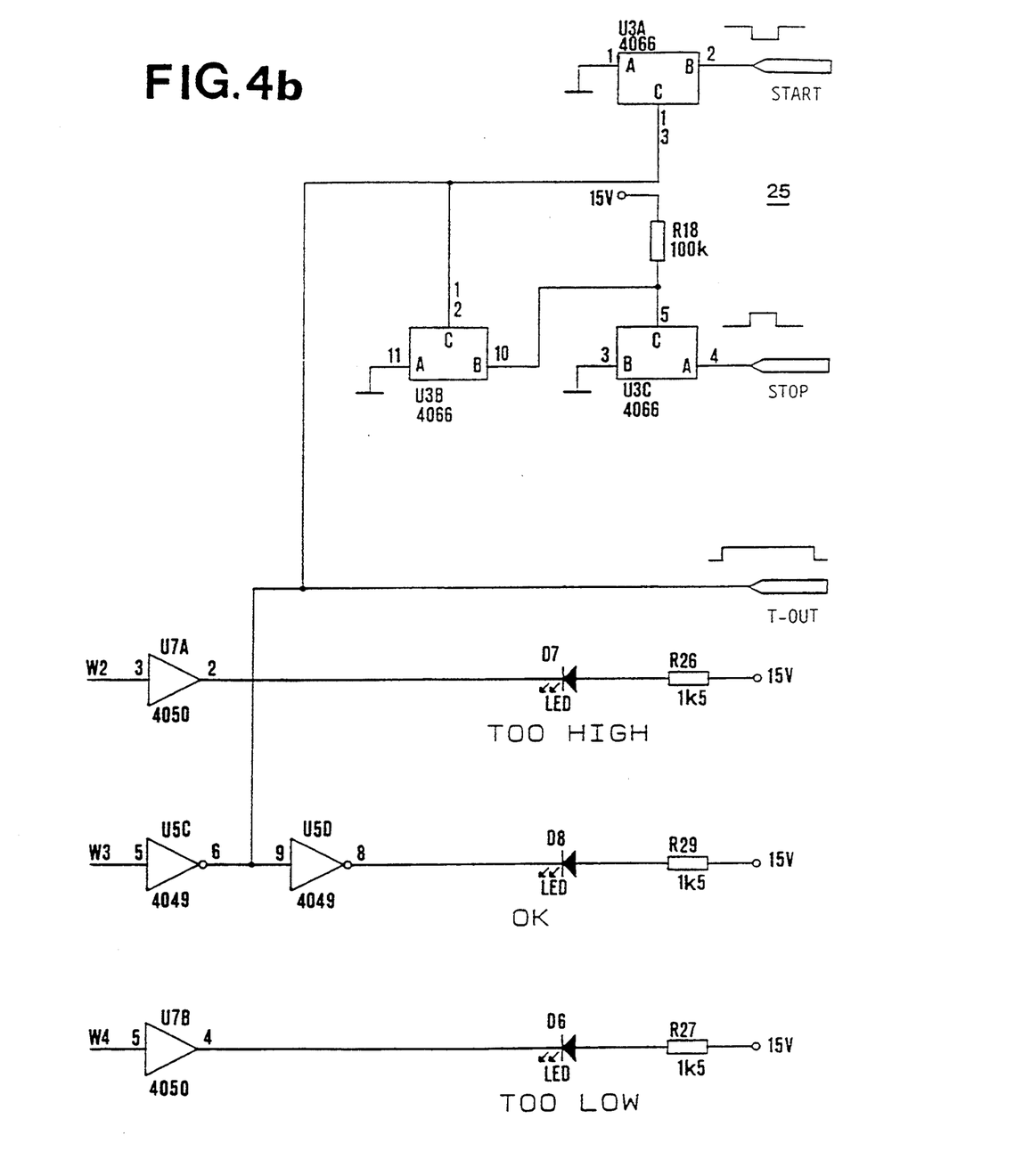

The time measuring unit (DTMU) comprises a mini-microphone 12 and an electronic circuit 13. This unit can also be provided with a digital display (not shown). The microphone transforms the sound waves into an alternating current. An example of electronic circuit is represented in FIG. 4. Said circuit processes the output signal from the microphone 12. The circuit comprises a high-pass filter 20, which filters out all frequencies below 100 Hertz. The filtered signal is sent to an amplifier 21 which amplifies the alternating current by a factor of about 50, from a few mV up to of the order of 200 mV. The amplified signal is then sent to a band-pass filter 22, which filters out all frequencies except those falling in a narrow band centred on 1650 Hertz and further amplifies the band-pass filtered signal. This signal is then transformed in circuit 23 into a digital voltage signal. This signal, which is dependent on loudness, is compared in two amplitude and frequency comparators 24 with a fixed threshold value. The comparators provide an output signal (T-out) for so long as the digital signal is above the threshold. The length of time for which an output is present at T-out is measured by an electronic clock. An alternative way of measuring the length of the note is to start and stop a clock by producing a positive signal at the beginning of the detected signal and at the end of the detected signal. This possibility is also represented in circuit 25 of the electronic scheme of FIG. 4. The length of the note is found to be directly proportional to the volume of air exhaled, and the length of the note can therefore be used to generate directly a value from this volume, which can be displayed.

By gradually opening the triangle shaped by-pass 5 using the turning cuff 6, the portion of the airflow passing through the sound generator, can be changed. By carrying out repeated measurements at different positions of the cuff, a plurality of curves can be generated, each corresponding to a different constant rate of exhalation. FIG. 1 shows three such curves. Each of said curves corresponds respectively to flow rates of 1 l/s, 2 l/s and 3 l/s. The envelopes of these curves is the peak-flow curve generated in the prior art.

It will be observed that the device according to the invention is simple in construction and does not include any movable components, so that its operation is not likely to be disturbed by collection of foreign matter. As a result a reliable operation may be expected without continual cleaning, this being particularly advantageous since the device is exposed to the patient mucus and saliva.

Sensitivity and reproducibility of the measurements have been evaluated by studying repeated measurements with different constant flow rates, experimentally produced and created by subjects breathing through the device. Reproducibility was calculated. It was in the range of 70 msec.

As to simplicity and economy of manufacture, all parts with the exception of the time measuring unit, can be made by moulding from plastics material, with the requirements for machining and other operations being reduced to a minimum. In addition, the embodiment described above can be made in a number of disconnectable sections, and thus can be readily disassembled for cleaning.

The scale on the connecting duct is preferably of curvilinear form, the range taking into account the use by children and adults of the device. This has been confirmed with an apparatus of the form just described having overall dimensions of about 12.9 cm length and 18 mm internal diameter, and a resonance chamber of the sound generator of 75 mm length and 15 mm diameter. As mentioned above, the dimensions of the chamber can be changed in order to modify the frequency of the note, with a corresponding change in the bandpass frequency.

The embodiment described can be modified in various ways. For example, the electronic circuit can be expanded by adding one or more memories for the purposes of extended home-monitoring, storing daily morning and evening readings, and storing pre- and post-medication measurements.

Furthermore, the electronic circuit of the device can be designed to produce, from different note lengths, and hence of different volumes, each corresponding to a specific isoflow, a plurality of parameters characterizing the exhalation of a person and hence the parameters of the flow-volume curve, such for example peak-flow, expiratory volumes at 0.5, 1, 1.5, 2, 3, 4 and 5 l/s, as well as expiratory flows at 75%, 50% and 25% of vital capacity. The device can be further provided with a sufficient number of storage means to store the signals corresponding to the calculated parameters, so as to be able to display, on a screen provided on the device, a complete set of consecutive lung function tests.

The device can include a housing containing a battery-driven microprocessor, designed in particular for the measurement of the exhaled air, and a screen disposed on the housing to display the measurements. The device can further include connecting means for its connection to a peripheral data collecting unit (PDCU), for communication via an interface with a personal computer or other like apparatus.

Further, the device can include means for its connection to a breath actuated inhalation device, by which patient can breathe in powder drugs, such as beta-stimulants, topic steroids or other anti-asthmatic products in order to check proper use of the therapy.

It is explained hereafter how the use of a whistle enables a constant flow rate to be achieved.

When the outlet 5 of the whistle is fully closed by the cuff 6, the whistle works exactly like a recorder. The only difference is that only one particular, well defined note (with a frequency of 1650 Hertz in the above described example) is produced. As long as the subject exhales through the whistle, initially started after full inspiration (at total lung capacity TLC) and ensures that a constant note is produced by the recorder, a constant flow rate is maintained. In pulmonary physiology, such a procedure is referred to as the generation of an isoflow. The constancy of this isoflow is ensured by the physiological feedback mechanism between the ear and the voluntary muscles necessary for the expiration. The isoflow produced with the by-pass outlet 5 closed is the lowest flow which can be registered with this device.

Exhaling from total lung capacity (TLC) down residual volume (RV) through the whistle with the by-pass outlet 5 open at a given position, a note is again generated, although some air is by-passed through the outlet. As the frequency of the whistle remains the same, a higher flow is needed to produce the same note as before. As before the note correlates closely with the flow which is blown through the whistle. The exact relationship between airflow producing a note and the position of the turning cuff on the scale on the connecting duct is defined by parallel measurements with a pneumotachograph placed in series with the whistle. Therefore, for each given opening of the triangle by-pass outlet, a well defined, corresponding airflow can be generated. The time for which the note is produced is directly related to the volume of air at a specific constant flow rate. By varying the by-pass outlet (and hence the isoflow) flow-volume curve data can be obtained. The measured time for which a note is produced and the given flow at a given position of the cuff enables the volume to be expired to be calculated from:

$$\text{volume} = \text{time (sec)} \times \text{flow (l/s)}.$$

By this procedure the different volumes in relation to the corresponding flow rates can be calculated.

According to another embodiment, the device can be arranged on an inversed manner, in order to measure inspiration airflows according to the same principles.

The use of the device according to the invention is not limited to the measure of flow/volume of pulmonary air exhaled by a person. As a matter of fact the device still performs all its functional features and advantages and usefulness should it be applied to the regulation of any airflow, whatever the context or apparatus concerned to be controlled.

We claim:

1. Medical device for measuring the flow-volume of pulmonary air breathed out by a subject, comprising a sound generator, an inlet in fluid communication with said sound generator and into which the subject blows, and a resonance chamber in fluid communication with said sound generator arranged to produce, under the effect of said blow, a note of predetermined frequency and amplitude, means for measuring the length of said note, and a by-pass outlet disposed between said inlet and said sound generator having means to adjustably and measurably vary the opening/closing of said by-pass outlet, the varying means reducing or increasing the amount of air which passes through said sound generator wherein by making measurements ar various openings of said by-pass outlet, the parameters of the expiratory flow-volume curve of the subject can be calculated.

2. The device according to claim 1, and further comprising means for modifying the length of the resonance chamber, said modifying means modifying the frequency of the note produced by the sound generator.

3. The device according to claim 1, and further comprising a housing containing a battery driven microprocessor which measures the exhaled air, and a screen disposed on the housing to display said measurements.

4. The device according to claim 1, and further comprising means for connecting the device to a peripheral data collecting unit (PDCU), adapted to communicate via an interface with a computer.

5. The device according to claim 1, and further comprising means for connecting the device to a breath actuated inhalation device, by which a patient can breathe in powdered drugs.

6. The device according to claim 1, including means for the regulation of the rate of airflow through said sound generator.

7. The device according to claim 1, wherein said inlet is a mouthpiece, and said sound generator further includes a lip and a time measuring unit, the mouthpiece and the sound generator being connected by a connecting duct on which is provided the by-pass outlet.

8. The device according to claim 1, wherein said inlet is a face mask.

9. The device according to claim 7, and further comprising a microphone intended to pick up said sound of predetermined frequency and amplitude, said microphone comprising means for producing a signal in an electric circuit comprising means for activating the time measuring unit, said unit measuring the length of time during which the sound generator produces said note and hence the length of time during which the signal is produced through the circuit.

10. The device according to claim 9, and further comprising at least one storage means receiving the value of said length of time and displaying said value on a screen.

11. The device according to claim 10, and further comprising a plurality of storage means receiving the values of the lengths of time of a plurality of note emissions and means for recalling and processing said values and arranging said values for monitoring the compliance of the patient.

12. The device according to claim 11, and further comprising means for producing, from different note lengths and hence from different volumes each corresponding to a specific isoflow, a plurality of parameters characterizing the exhalation of a person and hence the parameters of the flow-volume curve, including peak-flow, expiratory volumes at 0.5, 1, 1.5, 2, 3, 4 and 5 liters/second, as well as expiratory flows at 75%, 50% and 25% of vital capacity.

13. The device according to claim 12, and further comprising means for modifying the length of the resonance chamber of the sound generator, said modifying means modifying the frequency of the note produced by the sound generator.

14. The device according to claim 12, and further comprising a housing containing a battery driven microprocessor which measures the exhaled air, and a screen disposed on the housing to display said measurements.

15. The device according to claim 12, and further comprising means for connecting the device to a peripheral data collecting unit (PDCU), adapted to communicate via an interface with a computer.

16. The device according to claim 12, and further comprising means for connecting the device to a breath actuated inhalation device, by which a patient can breathe in powdered drugs.

17. The device according to claim 12, and further comprising means for storing the signals corresponding to at least one of the parameters characterizing a complete set of consecutive lung function tests.

18. The device according to claim 17, and further comprising means for modifying the length of the resonance chamber of the sound generator, said modifying means modifying the frequency of the note produced by the sound generator.

19. The device according to claim 18, and further comprising a housing containing a battery driven microprocessor which measures the exhaled air, and a screen disposed on the housing to display said measurements.

20. The device according to claim 19, and further comprising means for connecting the device to a peripheral data collecting unit (PDCU), adapted to communicate via an interface with a computer.

21. The device according to claim 20, and further comprising means for connecting the device to a breath actuated inhalation device, by which a patient can breathe in powdered drugs.

22. The device according to claim 21, including means for the regulation of the rate of airflow through said sound generator.

* * * * *

UNITED STATES PATENT AND TRADEMARK OFFICE
CERTIFICATE OF CORRECTION

PATENT NO. : 5,357,975
DATED : October 25, 1994
INVENTOR(S) : Richard Kraemer et al.

It is certified that error appears in the above-identified patent and that said Letters Patent is hereby corrected as shown below:

In column 6, line 46, the word "ar" should be changed to the word --at--.

Signed and Sealed this

Twenty-fourth Day of January, 1995

Attest:

BRUCE LEHMAN

*Attesting Officer*  *Commissioner of Patents and Trademarks*